(12) United States Patent
Ivosev et al.

(10) Patent No.: US 8,073,639 B2
(45) Date of Patent: Dec. 6, 2011

(54) METHOD FOR IDENTIFYING A CONVOLVED PEAK

(75) Inventors: Gordana Ivosev, Etobicoke (CA); Ronald Bonner, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 344 days.

(21) Appl. No.: 12/200,636

(22) Filed: Aug. 28, 2008

(65) Prior Publication Data

US 2009/0063102 A1    Mar. 5, 2009

Related U.S. Application Data

(63) Continuation-in-part of application No. 11/848,717, filed on Aug. 31, 2007, now Pat. No. 7,587,285.

(60) Provisional application No. 61/057,719, filed on May 30, 2008.

(51) Int. Cl.
   *G06F 17/00* (2006.01)
   *G06F 17/40* (2006.01)

(52) U.S. Cl. .......... 702/32; 702/30; 702/22; 250/339.07

(58) Field of Classification Search .................. 702/190, 702/22, 32, 30
   See application file for complete search history.

(56) References Cited

U.S. PATENT DOCUMENTS

| | | | |
|---|---|---|---|
| 4,807,148 A * | 2/1989 | Lacey | 702/32 |
| 6,873,915 B2 * | 3/2005 | Hastings | 702/22 |
| 6,934,638 B2 * | 8/2005 | Ito et al. | 702/22 |
| 2002/0173920 A1 * | 11/2002 | Xu et al. | 702/27 |
| 2003/0006770 A1 | 1/2003 | Smith | |
| 2005/0209525 A1 | 9/2005 | Bojovic et al. | |
| 2006/0088217 A1 * | 4/2006 | Akoa et al. | 382/191 |
| 2006/0257013 A1 | 11/2006 | Ramm et al. | |
| 2007/0278395 A1 * | 12/2007 | Gorenstein et al. | 250/282 |
| 2008/0272292 A1 * | 11/2008 | Geromanos et al. | 250/288 |

* cited by examiner

*Primary Examiner* — Hal Wachsman
(74) *Attorney, Agent, or Firm* — John R. Kasha; Kasha Law LLC

(57) ABSTRACT

A method for identifying a convolved peak is described. A plurality of spectra is obtained. A multivariate analysis technique is used to assign data points from the plurality of spectra to a plurality of groups. A peak is selected from the plurality of spectra. If the peak includes data points assigned to two or more groups of the plurality of groups, the peak is identified as a convolved peak. Principal component analysis is one multivariate analysis technique that is used to assign data points. A number of principal components are selected. A subset principal component space is created. A data point in the subset principal component space is selected. A vector is extended from the origin of the subset principal component space to the data point. One or more data points within a spatial angle around the vector are assigned to a group.

31 Claims, 15 Drawing Sheets

METHOD FOR IDENTIFYING A CONVOLVED PEAK

CROSS-REFERENCE TO RELATED APPLICATION

This application is a continuation-in-part application of U.S. patent application Ser. No. 11/848,717, filed Aug. 31, 2007, now U.S. Pat. No. 7,587,285. This application also claims the benefit of U.S. Provisional Patent Application No. 61/057,719 filed May 30, 2008. All of the above mentioned applications are incorporated by reference herein in their entireties.

INTRODUCTION

The present teachings can be used for data analysis to determine and interpret correlated variables. For example, multivariate statistical techniques can be applied to mass spectrometry (MS) data for use in biomarker discovery and metabolomics. MS can generate hundreds or thousands of variables, many of which are correlated, which complicates analysis. Although it is common to remove correlated variables prior to principal component analysis (PCA), their identification is valuable in the interpretation of mass spectral data since correlated peaks may be unpredictable fragments or may have known origins including, but not limited to, isotopes, adducts, and different charge states. Recognizing unpredictable fragments can help identify the compound that generated the spectrum.

A peak in a spectrum of data points can be the result of a single component or two or more components. A spectrum can be, for example, a mass spectrum of a sample. The components of a peak of a mass spectrum can, for example, include two or more compounds of the sample. If a peak is a result of two or more components, it can be referred at a convolved peak. Determining whether or not a peak is a convolved peak can be difficult. A convolved peak can appear in the spectrum as a single peak or as two or more overlapping peaks.

BRIEF DESCRIPTION OF THE DRAWINGS

The skilled artisan will understand that the drawings, described below, are for illustration purposes only. The drawings are not intended to limit the scope of the present teachings in any way.

Figure 1:
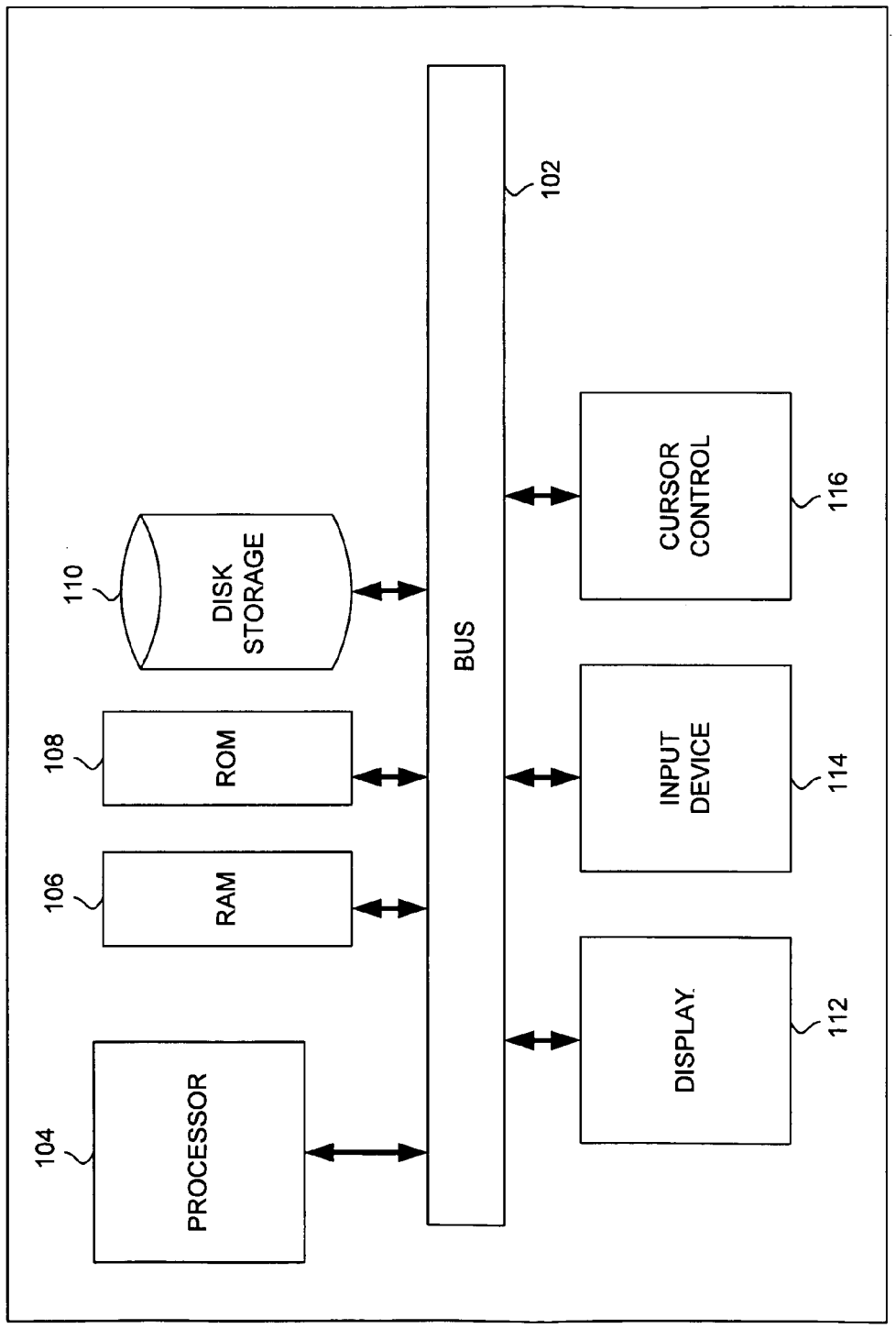
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

COMPUTER-IMPLEMENTED SYSTEM

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for determining base calls, and instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

PCA

Principal component analysis (PCA) is a multivariate analysis (MVA) tool that is widely used to help visualize and classify data. PCA is a statistical technique that may be used to reduce the dimensionality of a multi-dimensional dataset while retaining the characteristics of the dataset that contribute most to its variance. For this reason PCA is often used to pre-process data for techniques that do not handle high dimensionality data well such as linear discriminant analysis (LDA).

PCA can reduce the dimensionality of a large number of interrelated variables by using an eigenvector transformation of an original set of variables into a substantially smaller set of principal component (PC) variables that represents most of the information in the original set. The new set of variables is ordered such that the first few retain most of the variation present in all of the original variables. More particularly, each PC is a linear combination of all the original measurement variables. The first is a vector in the direction of the greatest variance of the observed variables. The succeeding PCs are chosen to represent the greatest variation of the measurement data and to be orthogonal to the previously calculated PC. Therefore, the PCs are arranged in descending order of importance. The number of PCs (n) extracted by PCA cannot exceed the smaller of the number of samples or variables. However, many of the variables may correspond to noise in the data set and contain no useful information.

PCA requires that data be presented in the form of a matrix (hereafter referred to as "the Input Matrix") where, for example, rows represent samples, columns represent variables, and an element or cell of the Input Matrix indicates the amount of that variable in a particular sample. Alternatively, the Input Matrix can include rows that represent variables, columns that represent samples, and elements that represent the amount of that variable in a particular sample. In the latter case, the processing described as applied to a loadings plot is instead applied to a scores plot. An Input Matrix can be decomposed into a series of score and loading vectors. The loading vectors indicate the contribution that each variable makes to a particular PC. The score vectors are a measure of the amount of each component in a particular sample.

Scores and loadings plots can be displayed where the axes represent two or more PCs, the samples are positioned according to their scores, and the variables are positioned according to the loadings. The scores reflect the amount of each PC present in the sample while the loadings indicate the importance of each variable to the PC.

Although PCA is an unsupervised technique requiring no knowledge of any sample groups, this information is frequently available and helps to interpret the scores plot. Knowledge about sample groups can, for example, help determine if the samples separate in an expected way or not. In contrast to the scores plot, the loadings plot can be very difficult to interpret, especially when there are many variables and none are dominant, or the data has been autoscaled to remove the effect of intensity.

Although it is common to remove correlated variables prior to PCA, their identification can help further interpretation. For example, in mass spectral data, correlated peaks may be unpredictable fragments or may have known origins including, but not limited to, isotopes, adducts, and different charge states. Recognizing unpredictable fragments can help identify the compound that generated the spectrum. Consequently, it can be beneficial to retain all variables extracted from the raw data, rather than removing the correlated variables before performing PCA, since this allows the loadings plots to be interpreted to find correlated features. Essentially, PCA is using the variables to separate and group the samples, but it is also using the samples to separate and cluster the variables. Once the correlated variables have been identified, they can be simplified in a number of ways including, for example, replacing a set of correlated variables with some group representation including, but not limited to, the most intense variable of the correlated variables, a new variable with the mean intensity of the correlated variables, or the sum of the correlated variables.

METHODS OF DATA PROCESSING

Figure 2:
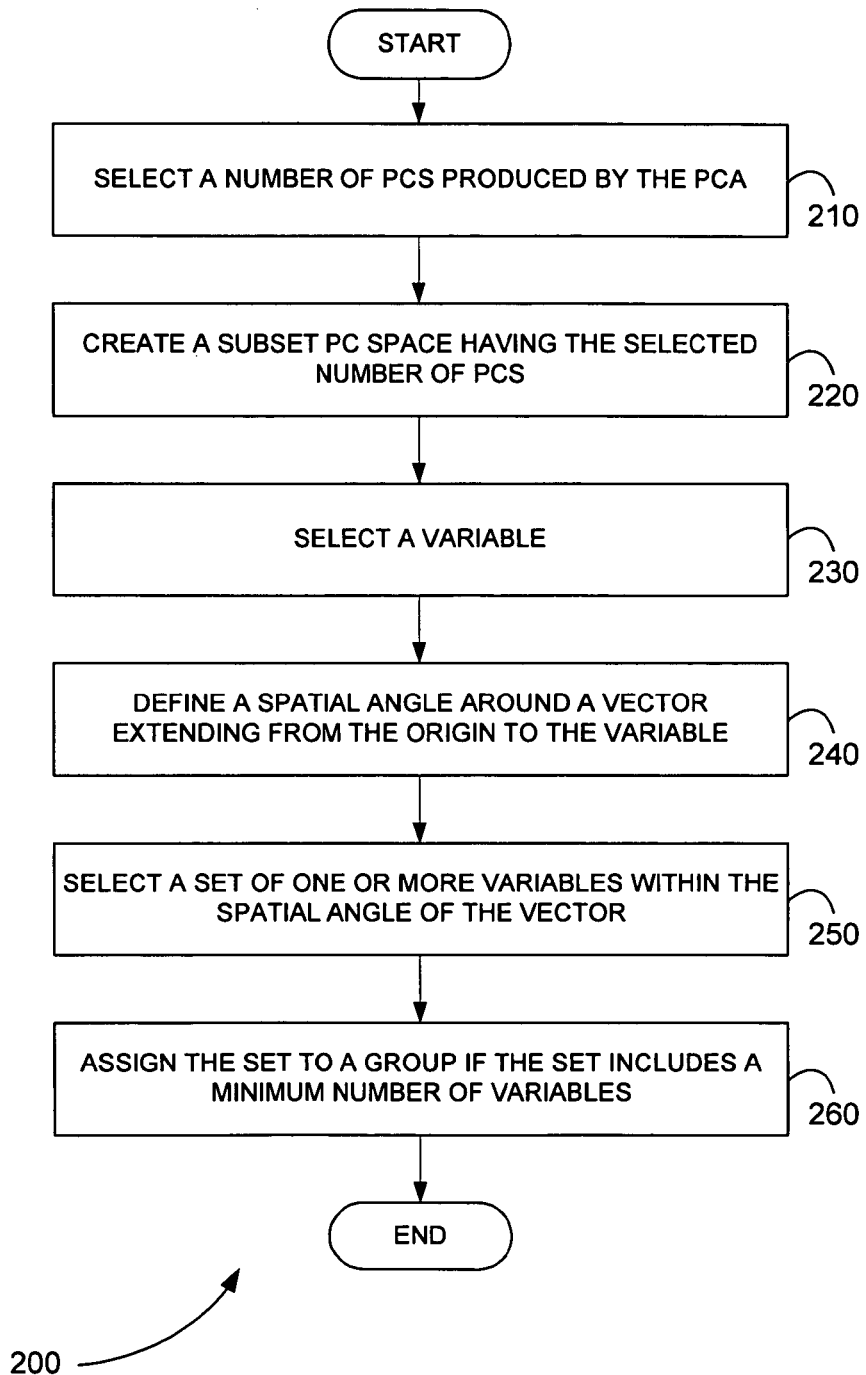
FIG. 2 is an exemplary flowchart showing a computer-implemented method for identifying correlated variables after PCA of a plurality of variables from a plurality of samples that is consistent with the present teachings.

FIG. 2 is an exemplary flowchart showing a computer-implemented method 200 for identifying correlated variables after PCA of a plurality of variables from a plurality of samples that is consistent with the present teachings.

In step 210 of method 200, a number of PCs produced by the PCA is selected. The number of PCs selected is, for example, less than the total number of PCs produced by the PCA. In various embodiments, the number of PCs selected is the smallest number that represents a specified percentage of the total variance.

In step 220, a subset PC space having the number of PCs selected is created.

In step 230, a variable is selected in the subset PC space. The variable selected is, for example, the variable that is furthest from the origin.

In step 240, a spatial angle is defined around a vector extending from the origin of the subset PC space to the selected variable.

In step 250, a set of one or more variables in the subset PC space is selected within the spatial angle of the vector. In various embodiments, if one or more variables within the set have a significance value less than a threshold value, then the one or more variables are not selected for the first set. The significance value is a minimum distance parameter, for example. The minimum distance parameter is a minimum distance from the origin, for example.

In step 260, the set is assigned to a group, if the set includes a minimum number of variables. The group identifies correlated variables, for example. The minimum number of variables is the number of correlated variables a group is expected to include, for example. The minimum number of variables can be, for example, one or a number greater than one.

In various embodiments, method 200 can also include calculating a second vector from the group, selecting a second set of one or more variables within the spatial angle of the second vector, and replacing the variables of the group with the variables of the second set, if the second set includes a minimum number of variables. The spatial angle of the second vector can be the same spatial angle defined in step 240, or the spatial angle of the second vector can be a spatial and that is different from the spatial angle defined in step 240. The second vector can be any linear or nonlinear combination of the variables in the group. For example, the second vector can be, but is not limited to, the arithmetic mean, a weighted mean, the median, or the geometric mean. In various embodiments, if one or more variables within the second set have a significance value less than a threshold value, then the one or more variables are not selected for the second set. The significance value is a minimum distance parameter, for example. The minimum distance parameter is a minimum distance from the origin, for example.

In various embodiments, method 200 can also include assigning a different symbol to each group that is identified. These symbols can then be used to visualize and interpret the loadings data.

In various embodiments, method 200 can also include assigning a set of variables that are anti-correlated to a group. This includes extending a line including the vector on an opposite side of the origin of the subset PC space, selecting a second set of one or more variables within the spatial angle of the line on the opposite side of the origin, and adding the second set to the group, if the set and the second set includes the minimum number of variables. In various embodiments, if one or more variables within the second set have a significance value less than a threshold value, then the one or more variables are not selected for the second set. The significance value is a minimum distance parameter, for example. The minimum distance parameter is a minimum distance from the origin, for example.

In various embodiments, method 200 can also include removing the set from further analysis, selecting a second variable in the PC space, selecting a second set of one or more variables within the spatial angle of a second vector extending from the origin of the subset PC space to the second variable, and assigning the second set to a second group of variables, if the second set includes the minimum number of variables. The second group identifies correlated variables also. The minimum number of variables can be, for example, one or a number greater than one. The second variable can, for example, be the unassigned variable that is furthest from the origin of the subset PC space.

In various embodiments, method 200 can also include calculating a third vector from the second group, selecting a third set of one or more variables within the spatial angle of the third vector; and replacing the variables of the second group with the variables of the third set, if the third set includes a minimum number of variables. The variables of the second group are assigned from the second set, for example. The third vector can be any linear or nonlinear combination of the variables in the second group. For example, the third vector can be, but is not limited to, the arithmetic mean, a weighted mean, the median, or the geometric mean. In various embodiments, one or more variables within the third set that have a significance value less than a threshold value are not selected. The significance value is a minimum distance parameter, for example. The minimum distance parameter is a minimum distance from the origin, for example. For visualization and interpretation purposes, a second and different symbol can be assigned to the second group.

In various embodiments, method 200 can also include assigning a set of variables that are anti-correlated to the second group. This includes extending a line comprising the second vector on an opposite side of the origin, selecting a third set of one or more variables within the spatial angle of the line on the opposite side of the origin, and adding the third set to the second group, if the set and the third set include the minimum number of variables. The minimum number of variables can be, for example, one or a number greater than one. In various embodiments, if one or more variables within the third set that have a distance from the origin less than a threshold value, then the one or more variables are not selected. The threshold value is a minimum distance parameter, for example.

In various embodiments, method 200 can also include sorting assigned groups. The sorting can be done, for example, by the largest distance from the origin in each group.

In various embodiments, method 200 can also include removing variables assigned to the group in step 260 from further analysis and repeating the steps of removing variables of a last assigned group from further analysis, selecting a new variable in the subset PC space, selecting a new set of one or more variables within the spatial angle of a new vector extending from the origin to the new variable, assigning the new set to a new group, if the new set includes the minimum number of variables, and removing variables of the new group from further analysis until the variables not assigned to a group do not exceed a threshold. The threshold can be, for example, a distance from the origin. Repeating these steps produces a plurality of groups of correlated variables, for example.

As mentioned above, PCA can be applied to data with a large number of variables and comparatively few samples (this data is said to have high dimensionality). Other analysis techniques require data where the number of samples exceeds the number of variables. Examples of these other analysis techniques include, but are not limited to, linear discriminant analysis (LDA) and independent component analysis (ICA). PCA, therefore, can be used to reduce the dimensionality of data for use in other analysis techniques, such as LDA and ICA. The reduced dimensions can be PCs or group representations of the groups. Using group representations is preferable, because groups are interpretable combinations of the original variables.

In various embodiments, method 200 can also include assigning a group representation to the group and using the group representation and the plurality of samples as input to a subsequent analysis technique. The group representation can include, but is not limited to, the most intense variable of the group, a variable with the mean intensity of the group, or the sum of the variables of the group. The subsequent analysis technique can include, but is not limited to, a clustering technique or a pattern recognition technique. The subsequent analysis technique can include, but is not limited to, LDA or ICA.

In various embodiments, method 200 can also include processing the group representation to generate new variables for input to the subsequent analysis technique. The subsequent analysis technique can include, but is not limited to, LDA, ICA, or PCA. Processing the group representation can include, but is not limited to, generating a nonlinear combination of the group representation and at least one other group representation. For example, a new variable can be a ratio of the group representation and another group representation.

In various embodiments of the present teachings, data scaling is performed prior to PCA processing so that, for example, high intensity variables do not dominate the analysis. One scaling technique is autoscaling, where the value for each variable is processed by first subtracting the mean of all values of the variable (i.e., mean centering) and then dividing by the variance of the variable. Autoscaling weights all variables equally and is appropriate where the variables are unrelated and can have widely different scales. However, when the variables are all of the same type (i.e., mass spectral or chromatographic peaks) and the more intense variables are more significant and less likely to be noise, Pareto scaling can be more advantageous. In Pareto scaling the mean centered values are divided by the square root of the variance. Pareto scaling reduces, but does not eliminate, the original intensity contribution and helps in interpreting loadings plots.

Figure 3:
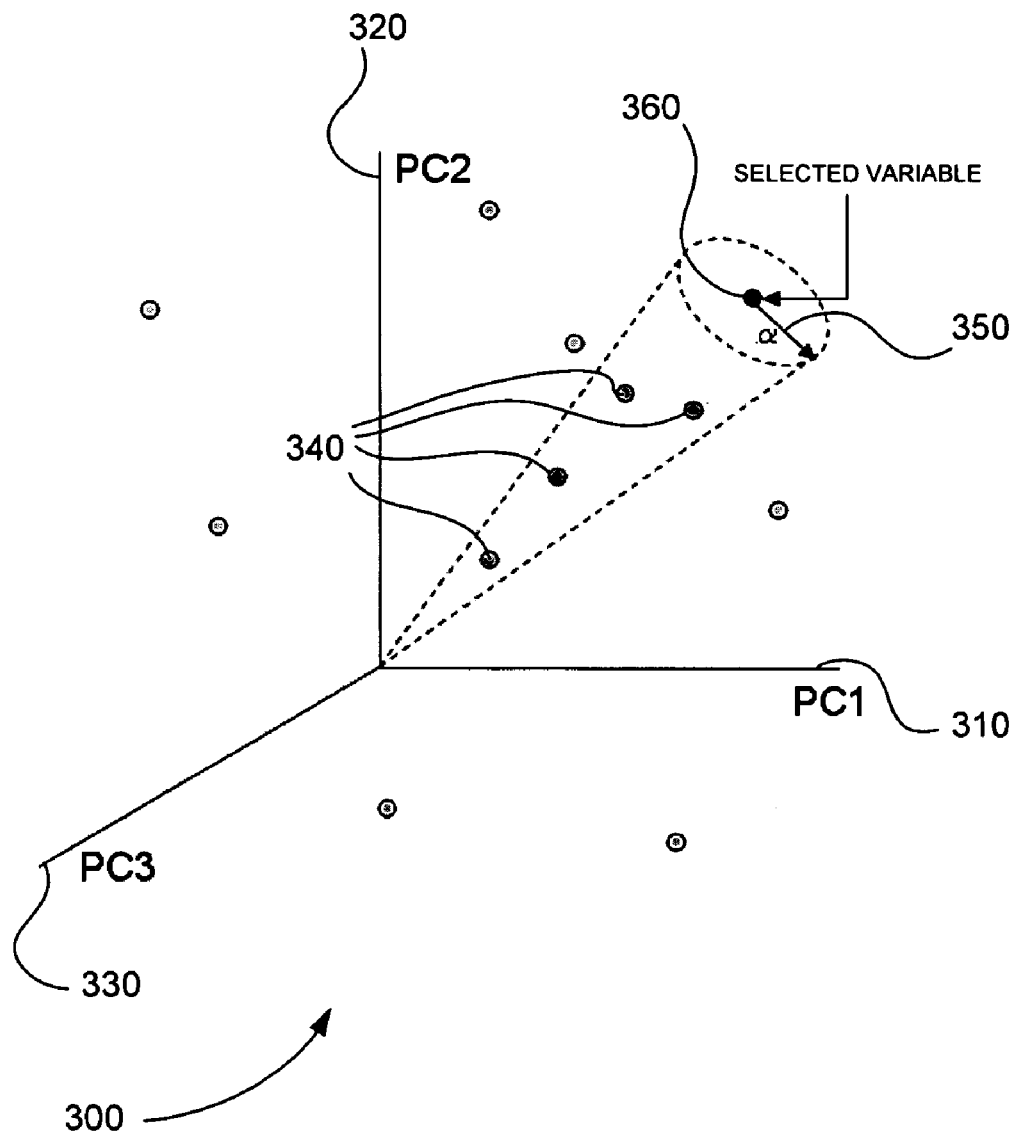
FIG. 3 is an exemplary illustration that shows how a set of one or more variables can be found within a spatial angle of a selected variable, in accordance with the present teachings.

FIG. 3 is an exemplary illustration 300 that shows how a set of one or more variables 340 can be found within a spatial angle 350 of a selected variable 360, in accordance with the present teachings. The three-dimensional PC space shown in FIG. 3 includes PCs PC1 310, PC2 320, and PC3 330. Variable 360 is selected in this three-dimensional PC space. Spatial angle 350 is defined around a vector extending from the origin to selected variable 360. One or more variables found within spatial angle 350 are selected as the set of one or more variables 340.

Figure 4:
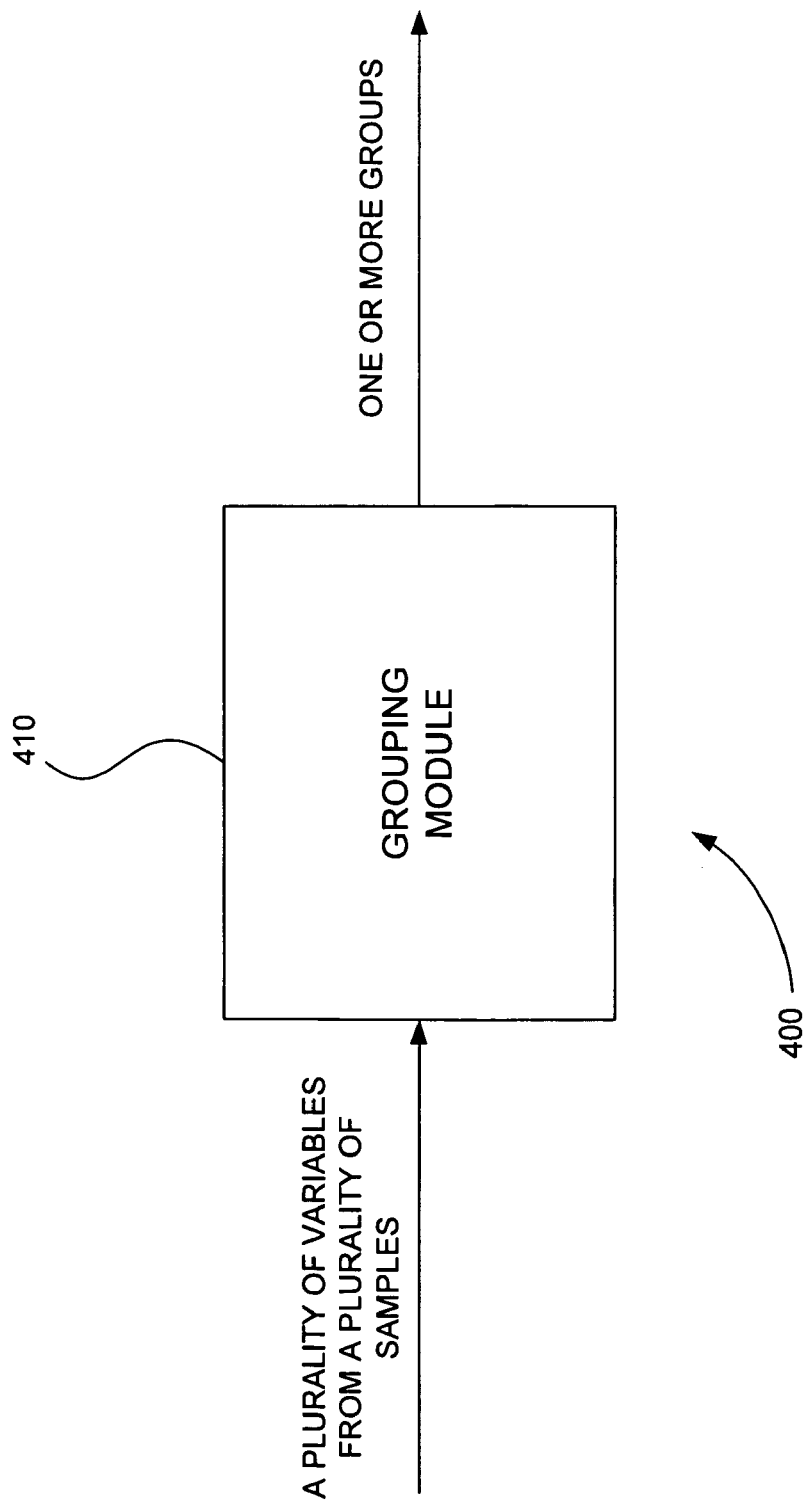
FIG. 4 is an exemplary schematic diagram showing a computing system for grouping variables after PCA of a plurality of variables from a plurality of samples produced by a measurement technique that is consistent with the present teachings.

FIG. 4 is an exemplary schematic diagram showing a computing system 400 for grouping variables after PCA of a plurality of variables from a plurality of samples produced by a measurement technique that is consistent with the present teachings. Computing system 400 includes grouping module 410. Grouping module 410 selects the number of PCs produced by the PCA, creates a subset PC space having the number of PCs, selects a variable, defines a spatial angle around a vector extending from an origin to the variable, selects a set of one or more variables within the spatial angle of the vector, and assigns the set to a group, if the set includes a minimum number of variables.

Figure 15:
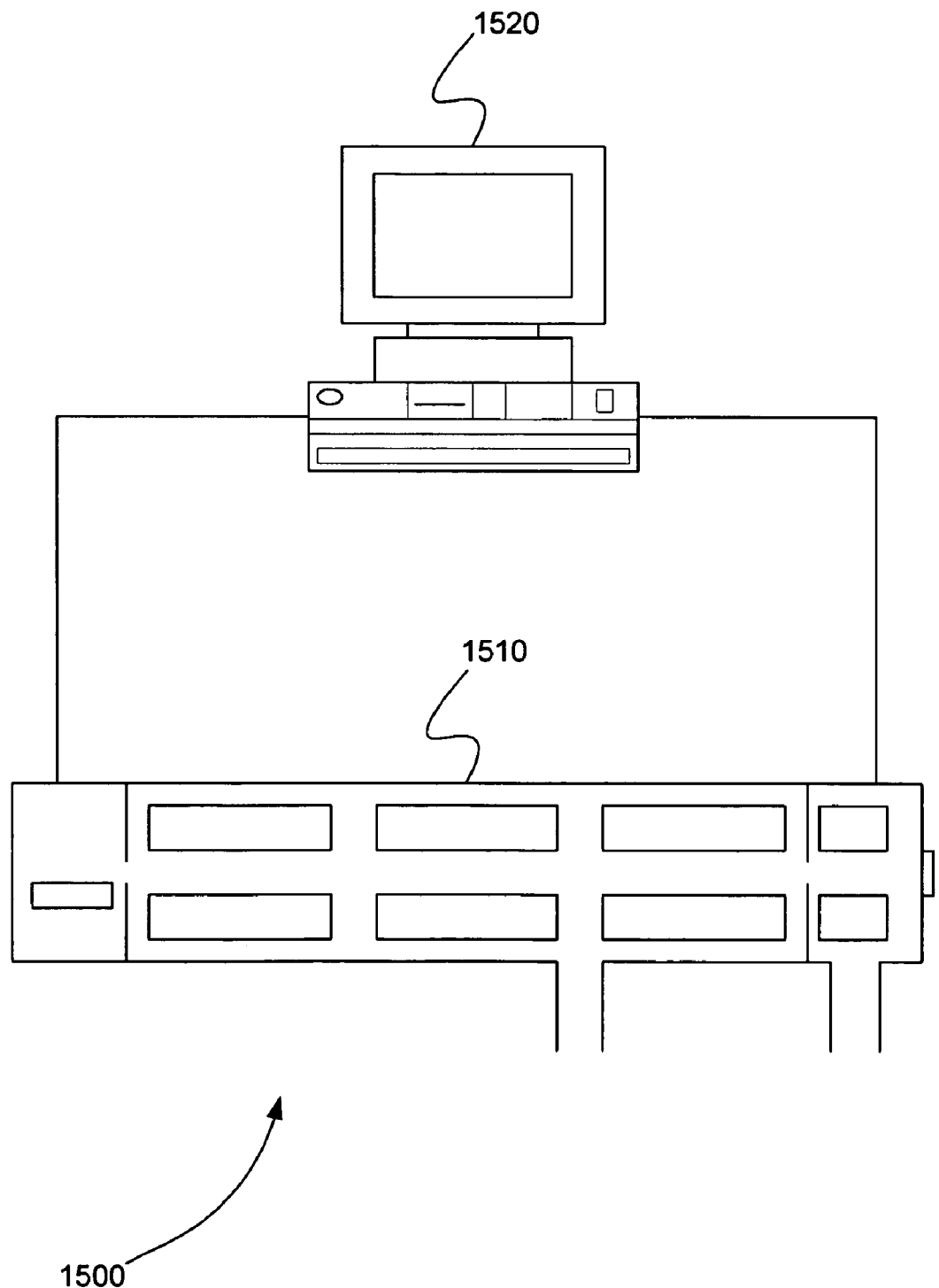
FIG. 15 is a schematic diagram of a system for identifying a convolved peak, in accordance with the present teachings.

In various embodiments of computing system 400, the plurality of variables can be generated using a measurement technique that generates more than one variable per constituent of a sample. The plurality of variables are generated using a measurement device, for example, as shown in FIG. 15. A measurement device can be, but is not limited to, a spectrometer or a mass spectrometer. Measurement techniques can include, but are not limited to, nuclear magnetic resonance, infra-red spectrometry, near infra-red spectrometry, ultra-violet spectrometry, Raman spectrometry, or mass spectrometry. In various embodiments the plurality of variables can be generated using a measurement technique that generates more than one variable per constituent of a sample combined with a separation technique. Separation techniques can include, but are not limited to, liquid chromatography, gas chromatography, or capillary electrophoresis.

In various embodiments, grouping module 410 can also select a second variable in the PC space, select a second set of one or more variables within the spatial angle of a second vector extending from the origin to the second variable, and assign the second set to a second group of variables, if the second set comprises the minimum number of variables.

Another computer-implemented method consistent with the present teachings is outlined below:

1. Perform PCA on all variables using Pareto scaling.
2. Determine the number of PCs (m) to be used. Using all n of the PCs extracted will exactly reproduce the original data. However, many of these PCs represent noise fluctuations in the data and can be ignored with no loss of information. Selecting m PCs effectively smoothes the data. Each variable is represented by a vector in this m-dimensional space.
3. Determine the target vector (t) that corresponds to the variable furthest from the origin. For this to be effective autoscaling is not used. Autoscaling is undesirable because it weights all variables, including small noise peaks, equally.
4. Define a spatial angle ($\alpha$) around this vector and find other data points (vectors) that are within that angle, optionally ignoring low intensity variables. If a second vector is x, then the angle ($\theta$) between x and the target vector can be found from:

$$x \cdot t = |x||t|\cos(\theta)$$

5. Calculate the mean of all selected vectors and repeat step 3 using the new mean vector and assign all selected variables to a group. "Re-centering" in this way fine tunes the orientation of the spatial angle and can be effective if the most intense variable is atypical in some way. For example, the profile may be distorted if the peak is saturated in the most concentrated samples. Since Pareto scaling has been used, calculating the mean vector also causes the lower intensity ions to have less effect on the result.

6. Repeat the process from step 3 ignoring previously grouped variables until there are no remaining variables with sufficient intensity.

Figure 5:
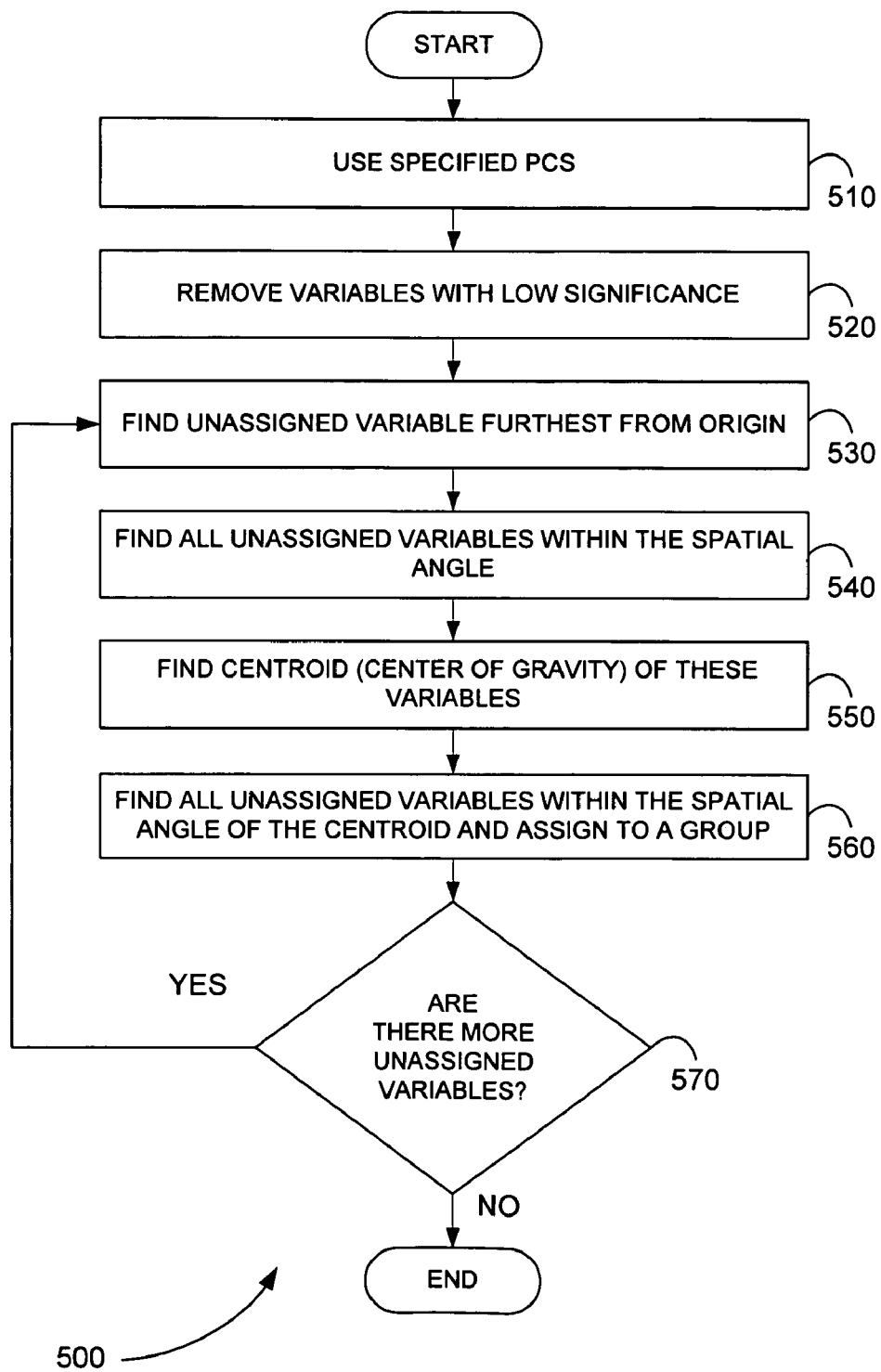
FIG. 5 is an exemplary flowchart showing a computer-implemented method that can be used for processing data in n-dimensional space and that is consistent with the present teachings.

FIG. 5 is an exemplary flowchart showing a computer-implemented method 500 that can be used for processing data in n-dimensional space and that is consistent with the present teachings.

In step 510 of method 500, PCA is performed on all variables and the specified subset of PCs is used.

In step 520, variables with low significance are removed. Filtering out variables that have low significance with respect to the selected scaling and PCA significance measure is optional. The same effect can be achieved by adding a step after grouping the variables and by using a different significance criterion. Another significance criterion that can be used is optical contrast, for example.

In step 530, a vector of an unassigned variable furthest from the origin is found.

In step 540, all vectors within a spatial angle of the vector are found.

In step 550, a mean of vectors within a spatial angle of the vector is found.

In step 560, all unassigned variables within the spatial angle of the mean are found and assigned to a group. Variables assigned to the group are then removed from processing.

In step 570, if any variables are left for processing, method 500 returns to step 530. If no variables are left for processing, method 500 ends.

The result of this processing is a number of groups of correlated variables that can be interpreted further, or group representations that can be used as input to subsequent analysis techniques. For visualization purposes, it is useful to identify grouped variables in a loadings plot by assigning a symbol to the group. Interpretation can be aided by generating intensity or profile plots for all members of a group.

Aspects of the present teachings may be further understood in light of the following examples, which should not be construed as limiting the scope of the present teachings in any way.

SOFTWARE EXAMPLE

Figure 6:
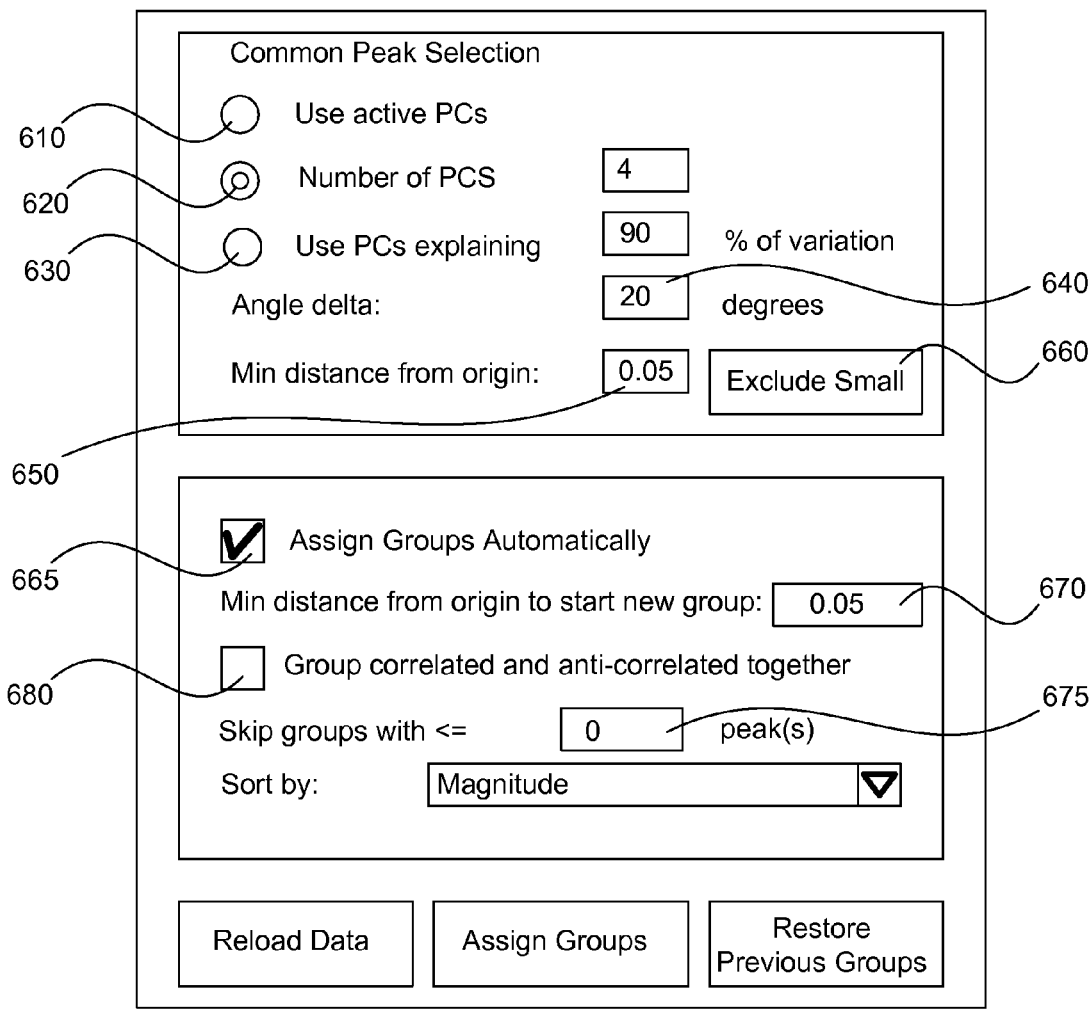
FIG. 6 is an exemplary image of a user interface for a software tool to perform variable grouping, in accordance with the present teachings.

FIG. 6 is an exemplary image of a user interface 600 for a software tool to perform variable grouping, in accordance with the present teachings. User interface 600 and the software tool can be used with existing viewing programs. One existing viewing program is, for example, MARKER-VIEW™ from Applied Biosystems/MDS Sciex.

The software tool can be run while an existing viewing program is running and after some data has been processed to generate scores and loadings plots. On starting, the software tool can interrogate the viewing program and obtain the loadings data. Following processing, the software tool can set a "group" column in the viewing program's loadings table so that the data points can be assigned symbols.

The number of PCs can be selected in three ways. First the number of PCs can be based on those currently displayed in the loadings plot by choosing selection 610. Second, a specific number of PCs can be entered using selection 620. Third, the software tool can select a number of PCs that explains a given amount of variance using selection 630. Selecting a number of PCs that represents a given amount of variance allows some control of the amount of noise ignored.

In field 640 of user interface 600, a user can enter a spatial angle parameter. In field 650, a user can enter a minimum intensity or minimum distance from the origin parameter. If desired, using "exclude small" button 660 on user interface 600, variables less than the minimum distance from the origin parameter can be marked as excluded so that they will not be used in any subsequent analysis.

Automatic or manual grouping can be selected using selection 665 from user interface 600. In the manual case, a user can select a variable of interest in the loadings plots and the software tool extracts a single group using that variable as the starting point. Selecting automatic processing, using selection 665 on user interface 600, allows a user to enter an additional threshold in field 670 for starting a group, which means that small variables can be considered if they are assigned to a group containing a larger variable, but small variables cannot be used to start a new group. User interface 600 can also include field 675 that requires a group to contain a minimum number of variables. Field 675 can be used if the data is expected to contain a number of correlated variables.

As described previously, correlated variables will lie substantially on the same straight line and will be on the same side of the origin of the loadings plot. The software tool can optionally include in the same group variables that are close to the extension of the line on the opposite side of the origin. These variables are anti-correlated. Inclusion of correlated and anti-correlated groups can be selected using selection 680 from user interface 600.

Finally, using selection 685 of user interface 600, a user can select to have the assigned groups sorted based on the intensity of the starting variable or based on the closeness in m-dimensional space to the first variable, for example.

Although user interface 600 shows three ways (i.e., selections 610, 620, and 630) of selecting the number of PCs, a software tool can use any known algorithm to determine how many are significant. In fact, the approach described in the present teachings can be used to iteratively determine the number of PCs to use and the groups. Typically increasing the number of PCs has little effect until the PCs are mostly due to noise, which can cause the number of groups to jump dramatically. As a result, the number of PCs used can be limited to a value less than the value causing the jump in the number of groups.

DATA EXAMPLES

In various embodiments of the present teachings, methods are described for analyzing PC loadings to determine related variables. For example, those showing similar expression patterns from a series of samples. These methods are illustrated using mass spectrometry (MS) data. However, these methods are applicable to other applications.

The data can be generated by analyzing each sample using a variety of spectrometric techniques, such as nuclear magnetic resonance (NMR), infra-red spectrometry (IR), near infra-red spectrometry (NIR), ultra-violet spectrometry (UV), Raman spectrometry, or mass spectrometry (MS). Analyses may also be performed using hyphenated techniques that couple one of the above spectrometric techniques with a chromatographic separation, such as liquid chromatography (LC), gas chromatography (GC), or capillary electrophoresis (CE). An exemplary hyphenated technique is liquid chromatography mass spectrometry (LC-MS). The patterns may be due to real biological variation that is of interest, such as changes due to disease or treatment with a therapeutic, or may be artifacts of the analysis that can be ignored. The variables found to be related can be interpreted to determine the compounds causing the pattern.

Another exemplary application for these methods can be finding peaks in data from a hyphenated technique. The data is generated using an exemplary hyphenated technique listed above by collecting a series of spectra from the effluent of a separation process. The patterns are due to the intensity profiles observed as peaks elute from the separation. Related variables will have the same pattern of variation and overlapping (unresolved) peaks can be determined. The variables found to be related can be interpreted to determine the compounds causing the pattern.

Another exemplary application for these methods can be interpreting tissue image data. The data is generated by any techniques that can give multiple measurements, such as a spectrum, at various points across a sample of biological tissue. The patterns are due to variations in the amount of compounds at different parts of the tissue and may correspond to different features or structures, such as organs and organelles. The variables found to be related can be interpreted to determine the compounds causing the pattern.

For MS data, the variables in the columns of the Input Matrix are generally mass bins or centroid values, for liquid chromatography coupled mass spectroscopy (LC-MS) the variables are characterized by mass-to-charge ratios (m/z) and retention time. In both cases, the data is aligned to ensure that the variable refers to the same signal in all samples.

Figure 7:
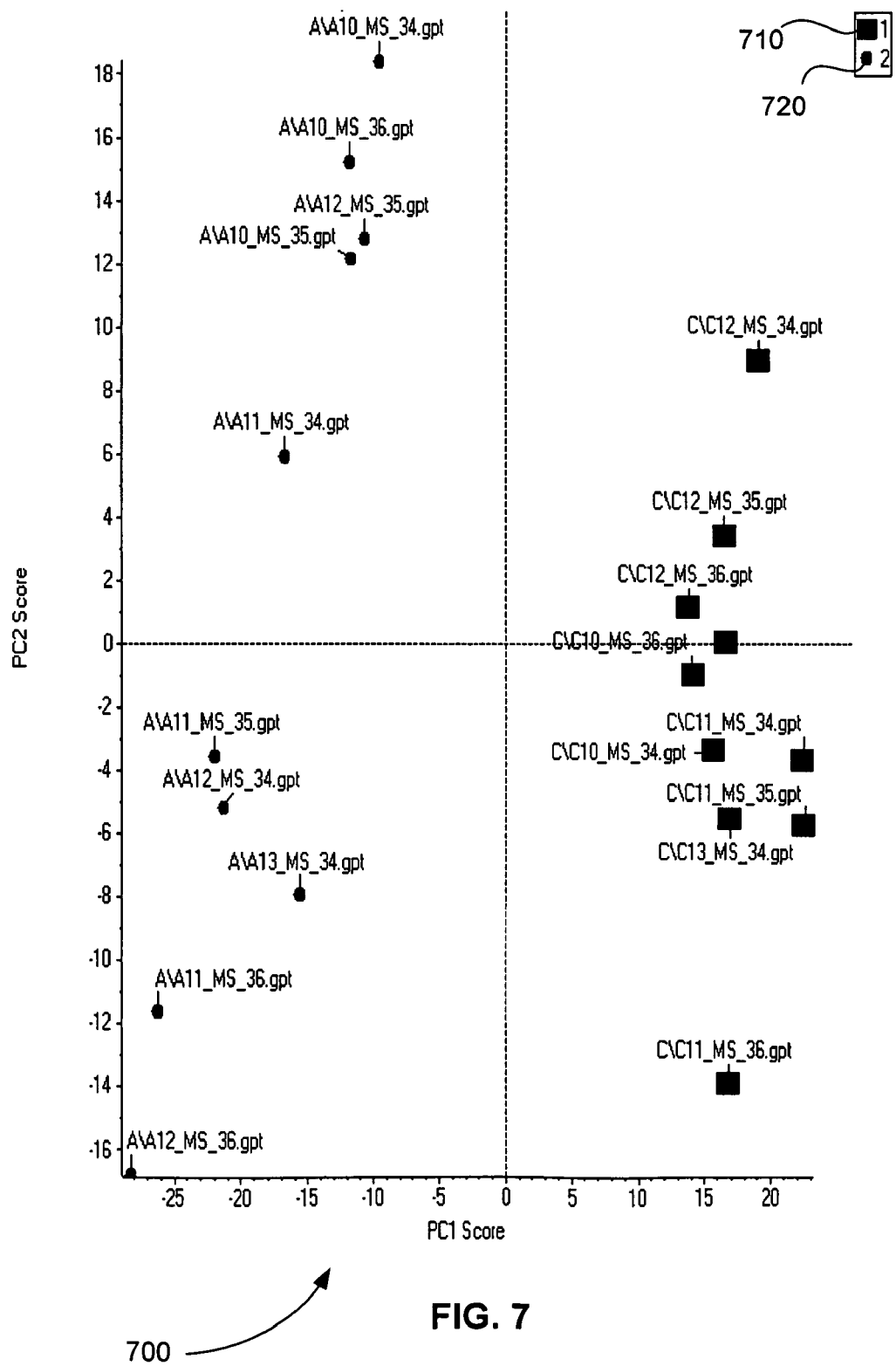
FIG. 7 is an exemplary scores plot of two principal components (PCs) for MS spectra data obtained after Pareto scaling and PCA, in accordance with the present teachings.

FIG. 7 is an exemplary scores plot 700 of two PCs for MS spectra data obtained after Pareto scaling and PCA, in accordance with the present teachings. The MS spectra data shown in FIGS. 7-9 was obtained using matrix-assisted laser desorption/ionization (MALDI). MALDI MS spectra data can be obtained, for example, using a mass spectrometer such as the APPLIED BIOSYSTEMS/MDS SCIEX TOF/TOF™ time of flight/time of flight mass spectrometer. PCA analysis and visualization of MALDI MS spectra data can be performed, for example, using MARKERVIEW™ software from Applied Biosystems/MDS Sciex.

FIG. 7 shows scores for samples from a protein digest with and without a spike of calibration mixture. Scores with a spike of a calibration mixture are shown with symbol 710 in FIG. 7. Scores without a spike of a calibration mixture are shown with symbol 720 in FIG. 7. Labels shown in FIG. 7 with symbols 710 and 720 are a combination of sample and sample group names.

As shown in FIG. 7, the spiked 710 samples and unspiked 720 samples are cleanly separated by the first PC, PC1, which explains the largest amount of variance. The spiked 710 samples have larger PC1 cores, indicating that they have relatively more of the variables with large, positive loadings, as shown in FIG. 8, than the unspiked 720 samples.

Figure 8:
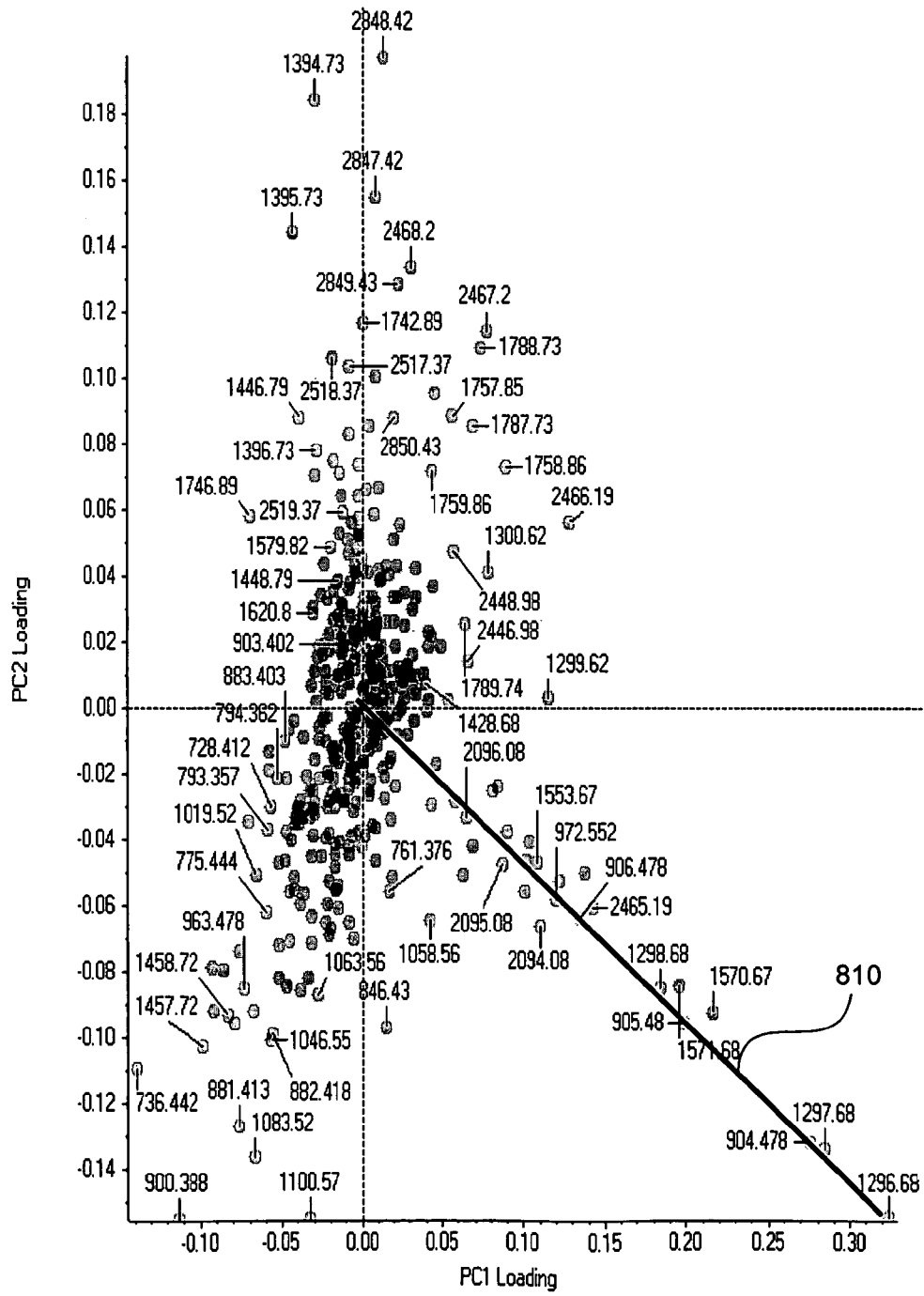
FIG. 8 is an exemplary loadings plot of two PCs for MS spectra data obtained after Pareto scaling and PCA, in accordance with the present teachings.

FIG. 8 is an exemplary loadings plot 800 of two PCs for MS spectra data obtained after Pareto scaling and PCA, in accordance with the present teachings. The labels in plot 800 correspond to the centroid m/z value of the variable.

In the example shown in FIG. 8, variables with the largest PC1 loadings tend to lie on straight line 810 that passes through the origin of the plot. This feature arises because these variables are correlated and show the same behavior across the sample set.

FIG. 8 also shows one benefit of Pareto scaling in interpreting the loadings plot. For any particular isotope cluster, the distance from the origin reflects the relative intensity of the peak. Thus it can be determined if the members of an isotope cluster have the same behavior as expected, which increases confidence in the observed separation/correlation.

Figure 9:
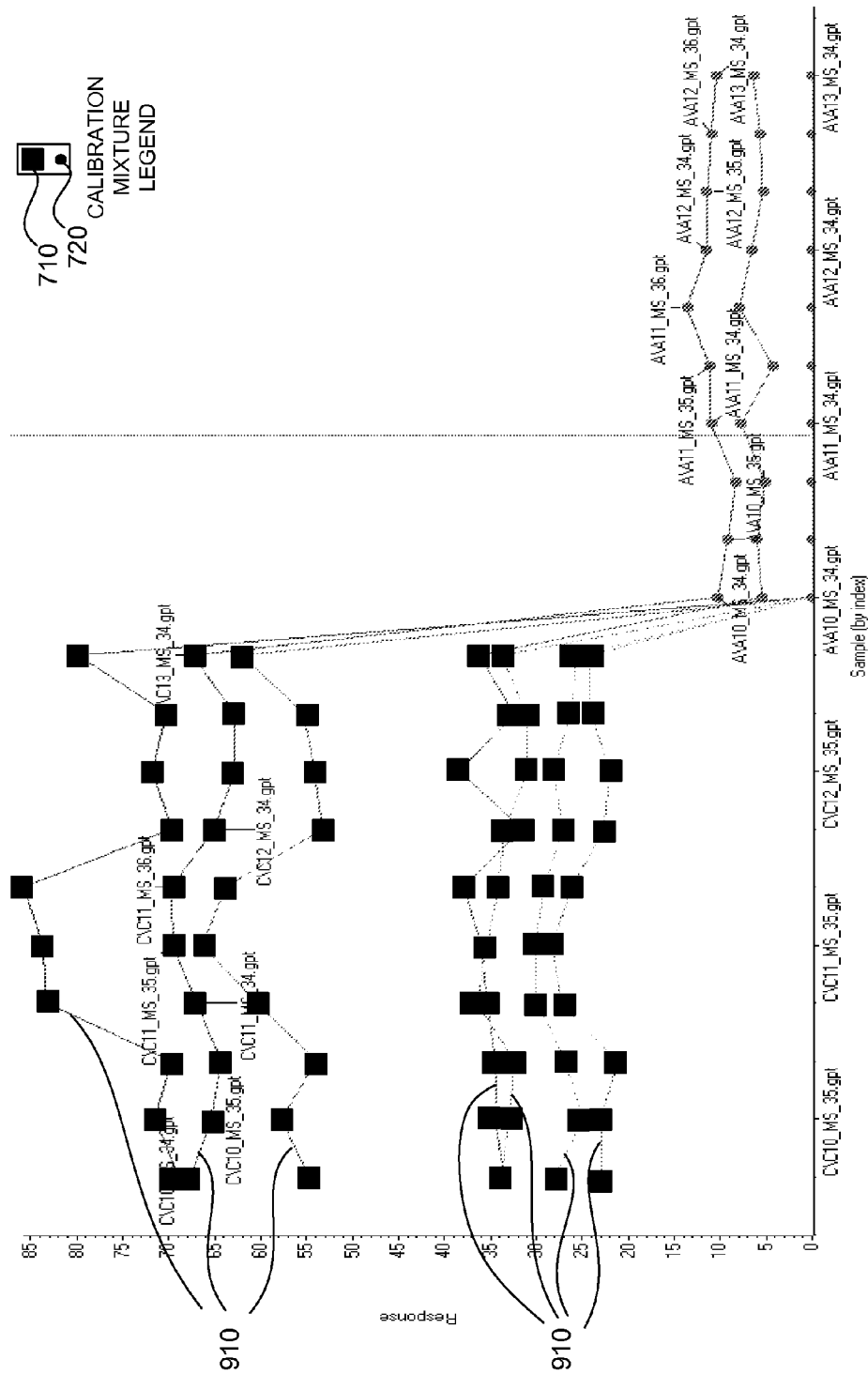
FIG. 9 is an exemplary profile plot of a few representative variables from MS spectra data obtained after Pareto scaling and PCA, in accordance with the present teachings.

FIG. 9 is an exemplary profile plot 900 of a few representative variables 910 from MS spectra data obtained after Pareto scaling and PCA, in accordance with the present teachings. A profile plot is a plot of the response of one or more variables as a function of a plurality of samples. Note that the correlation for variables 910 in FIG. 9 is not perfect due to noise. The slight variation in profiles causes the scatter around correlation line 810 shown in FIG. 8.

In various embodiments, components of a peak can be determined using a multivariate analysis technique on the data from a collection of spectra. If the peak contains data points that have different behaviors across the collection of spectra, the peak is determined to be a convolved peak.

Figure 10:
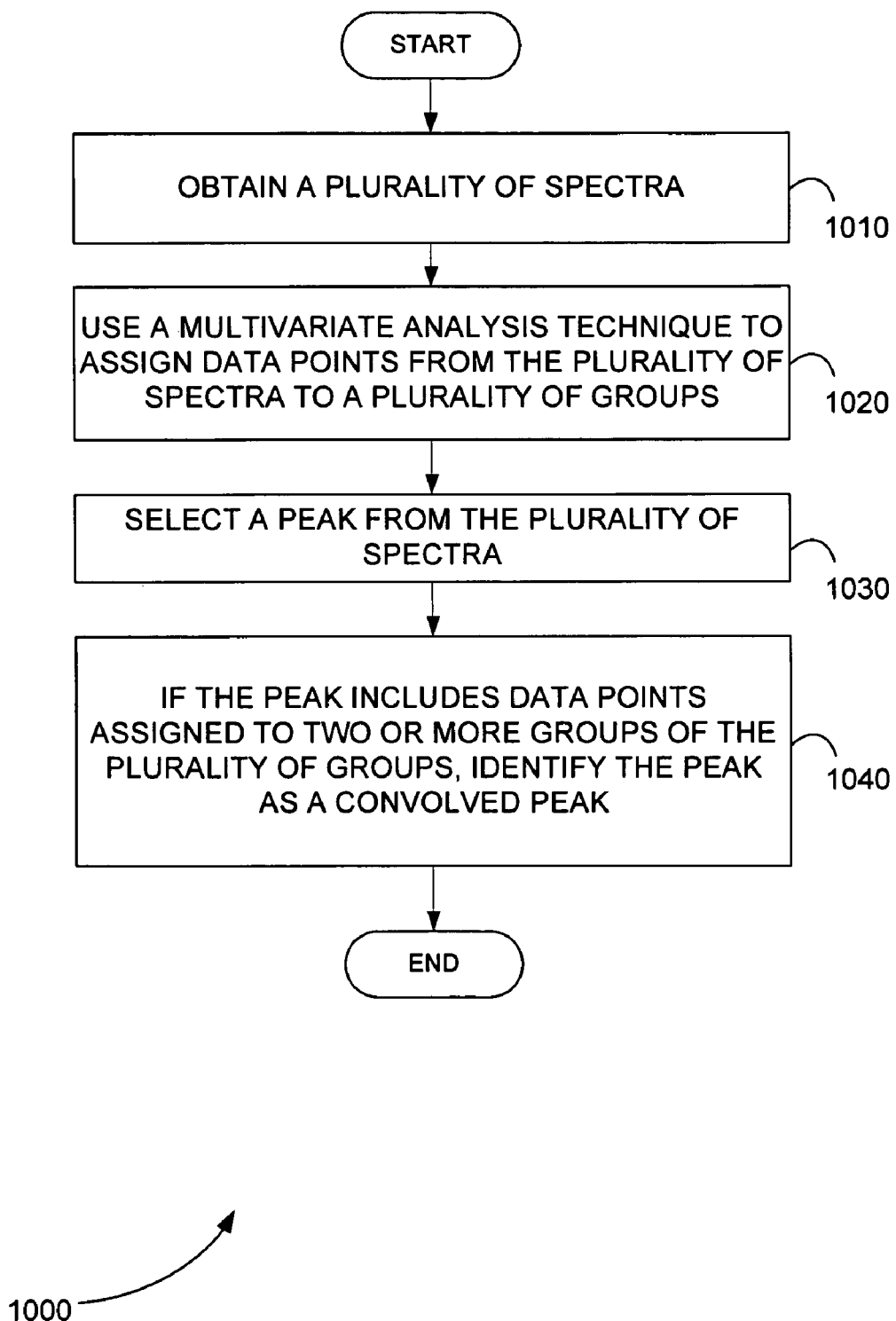
FIG. 10 is a flowchart showing a method for identifying a convolved peak, in accordance with the present teachings.

FIG. 10 is a flowchart showing a method 1000 for identifying a convolved peak, in accordance with the present teachings.

In step 1010 of method 1000, a plurality of spectra is obtained. The plurality of spectra is obtained from multiple samples, for example. In various embodiments, the plurality of spectra is obtained from a single sample. In various embodiments, obtaining the plurality of spectra can include, but is not limited to, performing spectroscopy, mass spectrometry, or nuclear magnetic resonance spectrometry.

In step 1020, a multivariate analysis technique is used to assign data points from the plurality of spectra to a plurality of groups.

In step 1030, a peak is selected from the plurality of spectra.

In step 1040, if the peak includes data points assigned to two or more groups of the plurality of groups, the peak is identified as a convolved peak.

In various embodiments of method 1000, the multivariate analysis technique can include an unsupervised clustering algorithm. An unsupervised clustering algorithm can include, but is not limited to, a self-organizing map, a k-means clustering algorithm, or a hierarchical clustering algorithm.

An unsupervised clustering algorithm can also include performing principal component analysis on the data points and using a method for identifying correlated data points after the principal component analysis to assign the data points to the plurality of groups. A number of principal components produced by the principal component analysis can be selected. A subset principal component space having the number of principal components can be created. A data point in the subset principal component space can be selected. A vector can be extended from an origin of the subset principal component space to the data point. One or more data points in the subset principal component space and within a spatial angle around the vector can be identified as a group of correlated data points. The group of correlated data points can then be assigned to the plurality of groups.

In various embodiments, method 1000 can also include processing one or more groups of the two or more groups of the plurality of groups to obtain information about a component of the peak. This information can include, but is not limited to, intensity data, mass data, chemical shift data, or wavelength data.

In various embodiments, method 1000 can be used with any spectroscopic technique and sample collection method.

In various embodiments, method 1000 can also include obtaining the plurality of spectra from analysis techniques including, but not limited to, liquid chromatography mass spectrometry analysis, gas chromatography mass spectrometry analysis, capillary electrophoresis mass spectrometry analysis, super-critical fluid chromatography mass spectrometry analysis, ion mobility mass spectrometry analysis, field asymmetric ion mobility mass spectrometry analysis, liquid chromatography nuclear magnetic resonance analysis, liquid chromatography ultraviolet spectroscopic analysis, gas chromatography infrared spectroscopic analysis, or spatial analysis.

In various embodiments, related data points can be determined by analyzing a number of samples. The related data points can be determined if they are correlated across the number of samples. For example, if the data points are part of a profile spectrum, a spectral peak may be found that appears to be a singlet, but actually has components that behave differently.

The samples may be a series of single spectra from a collection of real, physical samples. The spectra may be measured directly or obtained by combining all the spectra from the LCMS analyses of individual samples. The samples may be a series of spectra from the same sample, for example, spectra obtained across an LCMS peak. It is important that there is some variation of the ratio of the components of the convolved peaks among the spectra, but the exact form does not have to be known.

Figure 11:
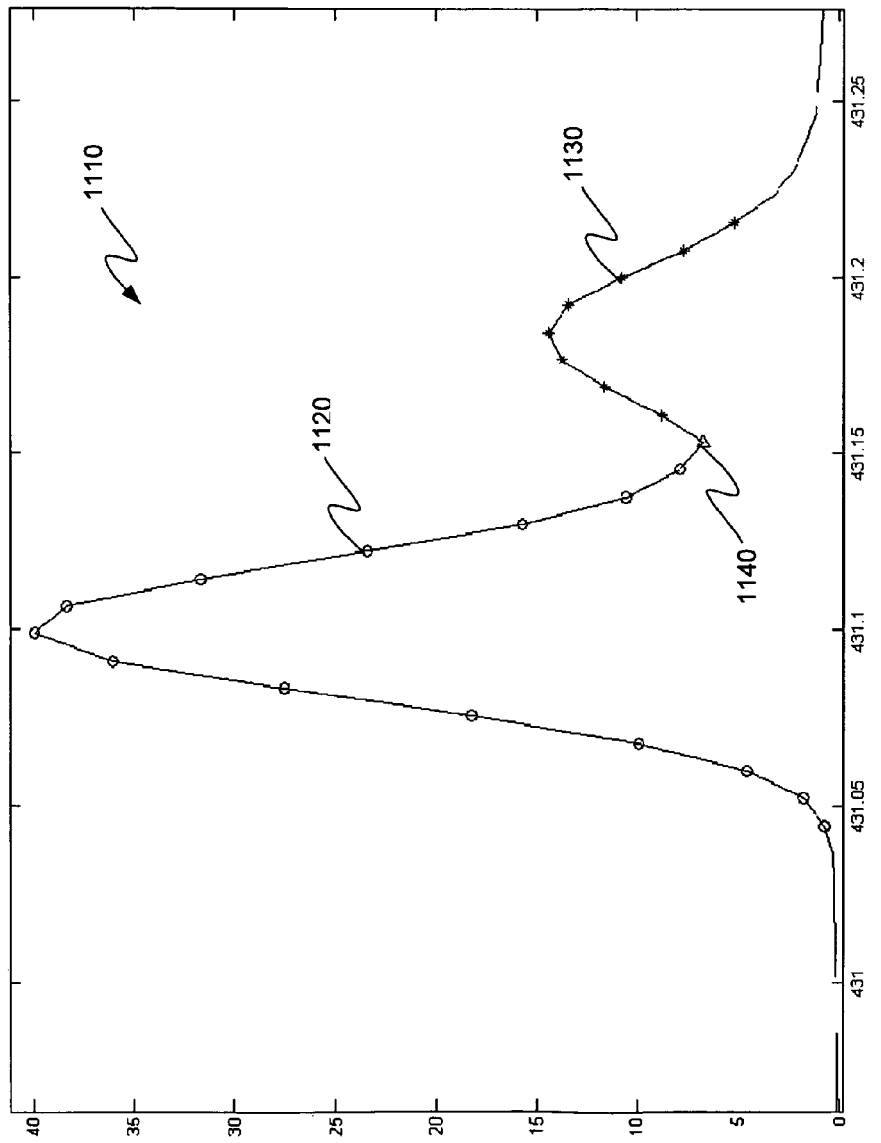
FIG. 11 is an exemplary plot of a convolved peak from a spectrum, in accordance with the present teachings.

FIG. 11 is an exemplary plot 1100 of a convolved peak 1110 from a spectrum, in accordance with the present teachings. The different symbols 1120, 1130, and 1140 correspond to data points of different groups assigned using a method for grouping variables after principal component analysis. The spectrum was obtained from a single sample, but the groups were determined by using the spectra from a number of samples to reveal different parts of each peak that have correlated behaviors.

Figure 12:
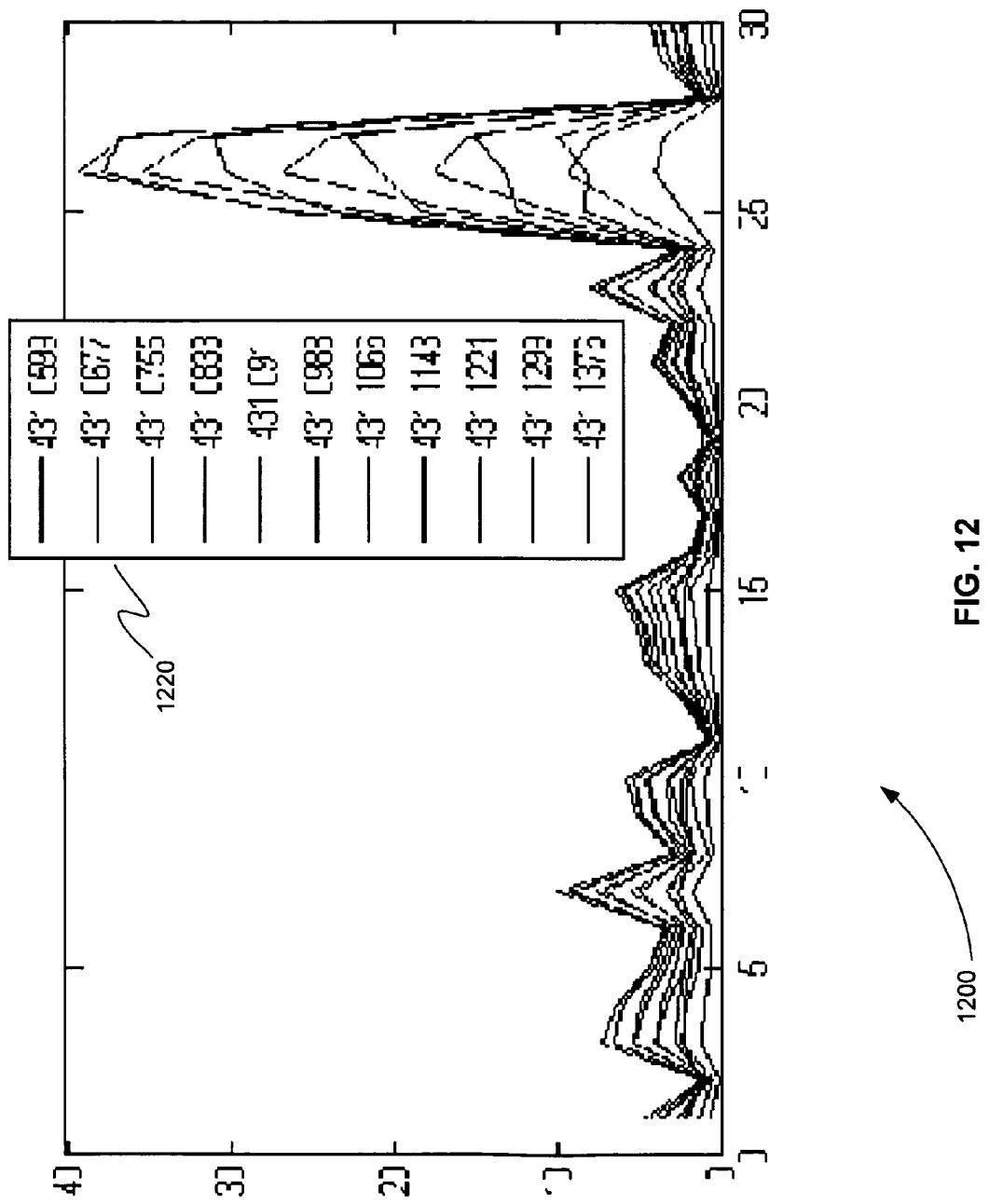
FIG. 12 is an exemplary plot of how intensity for each mass of a first group varies across samples, in accordance with the present teachings.

FIG. 12 is an exemplary plot 1200 of how intensity for each mass of a first group 1220 varies across samples, in accordance with the present teachings. The first group 1220 corresponds to symbols 1120 shown in FIG. 11.

Figure 13:
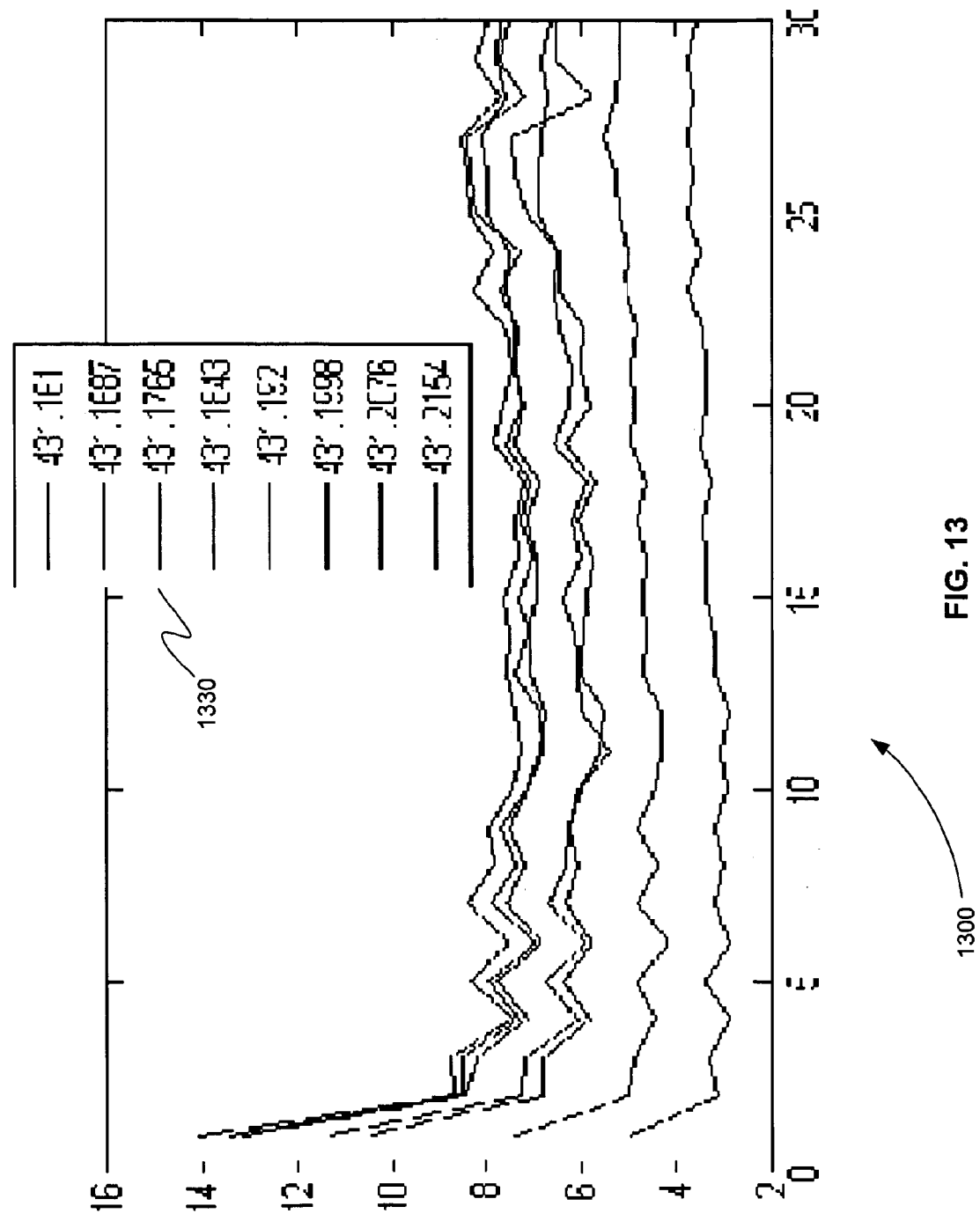
FIG. 13 is an exemplary plot of how intensity for each mass of a second group varies across samples, in accordance with the present teachings.

FIG. 13 is an exemplary plot 1300 of how intensity for each mass of a second group 1330 varies across samples, in accordance with the present teachings. The second group 1330 corresponds to symbols 1130 shown in FIG. 11.

Figure 14:
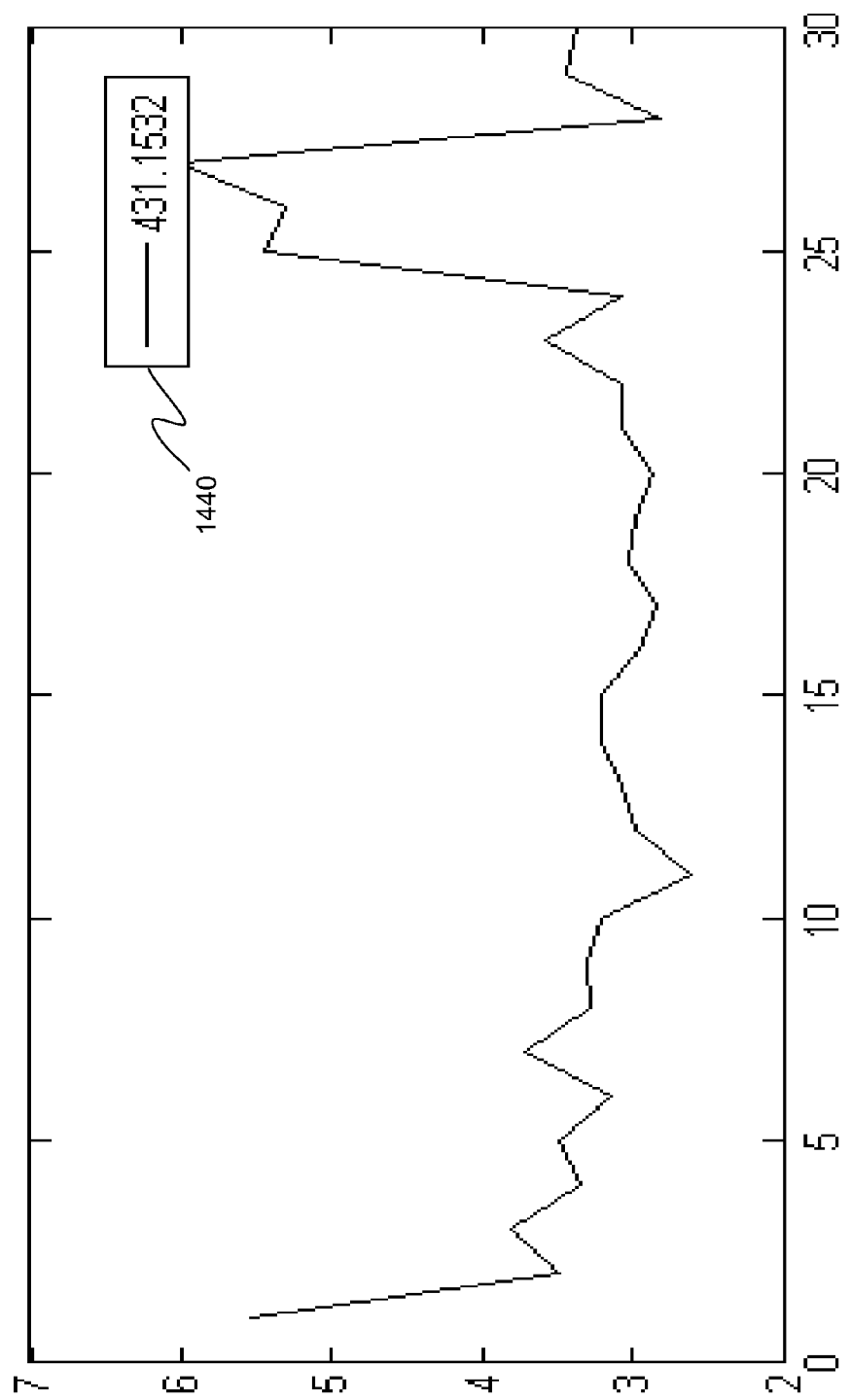
FIG. 14 is an exemplary plot of how intensity for each mass of a third group varies across samples, in accordance with the present teachings.

FIG. 14 is an exemplary plot 1400 of how intensity for each mass of a third group 1440 varies across samples, in accordance with the present teachings. The third group 1440 corresponds to symbol 1140 shown in FIG. 11.

A profile plot shows the response of a data point across samples. Plot 1200 in FIG. 12, plot 1300 in FIG. 13, and plot 1400 in FIG. 14 are profile plots of data points corresponding to symbols 1120, 1130, and 1140 in FIG. 11, respectively. Plot 1200 in FIG. 12 corresponding to symbols 1120 in FIG. 11 depicts a profile that is different from plot 1300 in FIG. 13 corresponding to symbols 1130 in FIG. 11. Data points represented by symbols 1120 and 1130 in FIG. 11 are present in all samples of plot 1200 in FIG. 12 and plot 1300 in FIG. 13, respectively, but show more intense values in particular samples. This indicates that they in fact belong to separate compounds.

The data point represented by symbol 1140 in FIG. 11 and plotted across samples in plot 1400 of FIG. 14 shows that this data point is likely present in the compound corresponding to the data points represented by symbol 1120 in FIG. 11 and the compound corresponding to the data points represented by symbol 1130 in FIG. 11, since plot 1400 of FIG. 14 represents a sum of plot 1200 of FIG. 12 and plot 1300 of FIG. 13. Hence the third group 1430 of FIG. 14 is a separate group but does not indicate the presence of an additional compound. Thus the groups associated with the same peak must be processed to determine the actual number of compounds present.

FIG. 15 is a schematic diagram of a system 1500 for identifying a convolved peak, in accordance with the present teachings. System 1500 includes measurement device 1510 and processor 1520. Measurement device 1510 can be, but is not limited to, a spectrometer or a mass spectrometer. Processor 1520 can be, but is not limited to, a computer, microprocessor, or any device that sends and receives control signals and data from measurement device 1510 and processes data. Measurement device 1510 that obtains a plurality of spectra. Processor 1520 uses a multivariate analysis technique to assign data points from the plurality of spectra to a plurality of groups, selects a peak from the plurality of spectra, and if the peak comprises data points assigned to two or more groups of the plurality of groups, identifies the peak as a convolved peak.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

What is claimed is:

1. A method for identifying a convolved peak, comprising:
    obtaining a plurality of spectra, wherein each spectrum of the plurality of spectra represents measurements from one or more samples;
    using a multivariate analysis technique that identifies two or more sets of correlated data points from the plurality of spectra and assigns each set of correlated data points to a group producing a plurality of groups;
    selecting a peak from the plurality of spectra; and
    if the peak comprises data points assigned to two or more groups of the plurality of groups, identifying the peak as a convolved peak.

2. The method of claim 1, wherein obtaining the plurality of spectra comprises obtaining the plurality of spectra from a plurality of samples.

3. The method of claim 1, wherein obtaining the plurality of spectra comprises obtaining the plurality of spectra from a single sample.

4. The method of claim 1, wherein the obtaining the plurality of spectra comprises performing mass spectrometry.

5. The method of claim 1, wherein the obtaining the plurality of spectra comprises performing nuclear magnetic resonance.

6. The method of claim 1, wherein the obtaining the plurality of spectra comprises performing spectroscopy.

7. The method of claim 1, wherein the multivariate analysis technique comprises an unsupervised clustering algorithm.

8. The method of claim 7, wherein the unsupervised clustering algorithm comprises a self-organizing map.

9. The method of claim 7, wherein the unsupervised clustering algorithm comprises a k-means clustering algorithm.

10. The method of claim 7, wherein the unsupervised clustering algorithm comprises a hierarchical clustering algorithm.

11. The method of claim 7, wherein the unsupervised clustering algorithm comprises principal component analysis.

12. The method of claim 11, wherein the unsupervised clustering algorithm further comprises
    selecting a number of principal components produced by the principal component analysis,
    creating a subset principal component space having the number of principal components, selecting a data point in the subset principal component space, extending a vector from an origin of the subset principal component space to the data point, identifying one or more data points in the subset principal component space and within a spatial angle around the vector as a group of correlated data points, and assigning the group of correlated data points to the plurality of groups.

13. The method of claim 1, further comprising processing one or more groups of the two or more groups to obtain information about a component of the peak.

14. The method of claim 13, wherein the information comprises intensity data.

15. The method of claim 13, wherein the information comprises mass data.

16. The method of claim 13, wherein the information comprises chemical shift data.

17. The method of claim 13, wherein the information comprises wavelength data.

18. The method of claim 1, wherein obtaining the plurality of spectra comprises liquid chromatography mass spectrometry analysis.

19. The method of claim 1, wherein obtaining the plurality of spectra comprises gas chromatography mass spectrometry analysis.

20. The method of claim 1, wherein obtaining the plurality of spectra comprises capillary electrophoresis mass spectrometry analysis.

21. The method of claim 1, wherein obtaining the plurality of spectra comprises super-critical fluid chromatography mass spectrometry analysis.

22. The method of claim 1, wherein obtaining the plurality of spectra comprises ion mobility mass spectrometry analysis.

23. The method of claim 1, wherein obtaining the plurality of spectra comprises obtaining the plurality of spectra from field asymmetric ion mobility mass spectrometry analysis.

24. The method of claim 1, wherein obtaining the plurality of spectra comprises liquid chromatography nuclear magnetic resonance analysis.

25. The method of claim 1, wherein obtaining the plurality of spectra comprises liquid chromatography ultraviolet spectroscopic analysis.

26. The method of claim 1, wherein obtaining the plurality of spectra comprises gas chromatography infrared spectroscopic analysis.

27. The method of claim 1, wherein obtaining the plurality of spectra comprises spatial analysis.

28. A non-transitory computer-readable storage medium whose contents include a program with instructions being executed on a processor so as to realize a method for identifying a convolved peak, the instructions comprising:

obtaining a plurality of spectra, wherein each spectrum of the plurality of spectra represents measurements from one or more samples;

using a multivariate analysis technique that identifies two or more sets of correlated data points from the plurality of spectra and assigns each set of correlated data points to a group producing a plurality of groups;

selecting a peak from the plurality of spectra; and if the peak comprises data points assigned to two or more groups of the plurality of groups, identifying the peak as a convolved peak.

29. A system for identifying a convolved peak, comprising:

a measurement device that obtains a plurality of spectra, wherein each spectrum of the plurality of spectra represents measurements from one or more samples;

a memory on which instructions are stored; and a processor that reads the instructions from the memory and executes the instructions, the instructions comprising using a multivariate analysis technique that identifies two or more sets of correlated data points from the plurality of spectra and assigns each set of correlated data points to a group producing a plurality of groups;

selecting a peak from the plurality of spectra, and if the peak comprises data points assigned to two or more groups of the plurality of groups, identifying the peak as a convolved peak.

30. The system of claim 29, wherein the measurement device comprises a spectrometer.

31. The system of claim 29, wherein the measurement device comprises a mass spectrometer.

* * * * *